United States Patent [19]

Saitoh et al.

[11] 4,042,332
[45] Aug. 16, 1977

[54] SEPARATION METHOD OF METHANE FROM OTHER HYDROCARBONS THAN METHANE

[75] Inventors: Osamu Saitoh; Masakatu Imaki, both of Kyoto; Hazime Asami, Higashiosaka, all of Japan

[73] Assignee: Horiba, Ltd., Japan

[21] Appl. No.: 643,952

[22] Filed: Feb. 10, 1976

[30] Foreign Application Priority Data

Dec. 23, 1974  Japan .................................. 49-50178

[51] Int. Cl.² .................... G01N 31/10; G01N 31/12; B01D 53/16
[52] U.S. Cl. .............................. 23/232 R; 23/230 PC; 23/254 E; 23/232 E; 23/232 C; 55/74
[58] Field of Search ............. 23/232 C, 232 E, 232 R, 23/254 E, 254 R, 253 PC, 230 PC; 55/135, 74; 260/449 M

[56] References Cited

U.S. PATENT DOCUMENTS

| 3,230,046 | 1/1966 | Beroza | 23/232 R |
|---|---|---|---|
| 3,304,159 | 2/1967 | Hinsvark | 23/232 X |
| 3,304,170 | 2/1967 | Hinsvark | 23/232 X |
| 3,372,994 | 3/1968 | Giuffrida | 23/254 E |
| 3,440,017 | 4/1969 | Palmer | 23/232 E |
| 3,460,909 | 8/1969 | Gayle | 23/254 E |
| 3,753,653 | 8/1973 | Brieva | 23/232 C |
| 3,762,878 | 10/1973 | Villalobos | 23/232 C |
| 3,847,546 | 11/1974 | Paul | 23/230 PC |

Primary Examiner—R.E. Serwin
Attorney, Agent, or Firm—Wenderoth, Lind & Ponack

[57] ABSTRACT

A method for the separation of methane from a gaseous mixture containing methane and at least one of ethane and propane which comprises a. simultaneously passing said gaseous mixture and oxygen over a catalyst comprising platinum on an active carbon carrier;
b. selectively oxidizing the ethane and propane in said gaseous mixture at a temperature of about 170° C and
c. recovering methane from said mixture.

7 Claims, 4 Drawing Figures

SEPARATION METHOD OF METHANE FROM OTHER HYDROCARBONS THAN METHANE

DETAILED DESCRIPTION OF THE INVENTION

BACKGROUND OF THE INVENTION

In the field of measuring the amount of hydrocarbons, which cause photochemical smog, it has been known to use a total hydrocarbon content analysis method such as the FID (flame-ionization detecting method). However, it is desired to employ continuous measurement of the concentrations of other hydrocarbons than methane as a hydrocarbon measuring method for monitoring air-pollution, since it has been revealed that methane does not take part in formation of photochemical smog to the extent that other hydrocarbons do.

The present invention relates to a method for the separation of methane from hydrocarbons other than methane which can be employed in hydrocarbon-detecting device and the like.

It is also well-known that there is a remarkable difference in oxidation temperature between the group methane, ethane and propane and the other hydrocarbons, other than the above three types of hydrocarbons. Consequently, it is possible to employ this difference in oxidation reaction temperature to separate methane, ethane and propane from these other hydrocarbons.

However, it is very difficult to separate methane from ethane and propane by this method because of their similarity in chemical activity.

It is strongly desired to develop a method for separating methane from ethane and propane in order to obtain greater precision in a hydrocarbon measuring device for monitoring atmospheric air pollution, since propane gas has been commonly used as a domestic and automobile fuel.

SUMMARY OF THE INVENTION

The invention employs a particular catalyst of high absorbing power, such as active carbon particles whose outer surface and inner surface pores are coated with platinum. It has been noted by the present invention that there is a difference in the amount of methane and either ethane or propane, absorbed on the catalyst carrier, that is, the difference in retention times of these hydrocarbons on the catalyst carrier, and they have made the present invention based on this observation. In the practice of the invention, there is employed a catalyst of high absorbing power such as one consisting of active carbon coated with platinum or additionally, containing a small amount of palladium and copper oxide. The separation procedure of methane from ethane and propane is carried out based on a difference in absorption on the above catalyst between methane and either ethane or propane.

DETAILED DESCRIPTION OF THE PREFERRED EMBODIMENT

Figure 1:
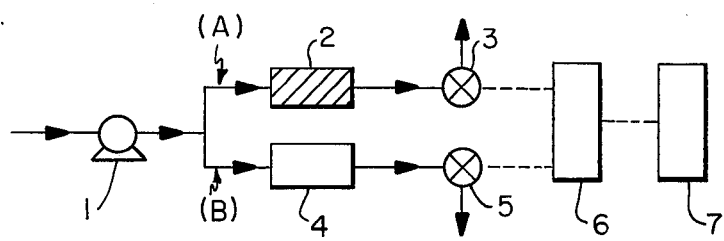
FIG. 1 is a flow-sheet which illustrates an example of the present invention.

Examples of the present invention are described and explained in details, hereafter. Referring to the attached drawings, in FIG. 1, 1 is a suction type pump, by which air (a gas sample to be analysed) is continuously sucked in from the atmosphere. The air is divided into two passages (A, B) continuously. In one passage (A), there is placed a catalyst vessel 2 (details of the vessel will be explained hereafter), in which hydrocarbons other than methane are subjected to oxidation, methane being free from oxidation and being sent to a FID detector 3 to measuring the methane content of the sample. Air which has been sent into the passage (B) is carried into the gas flow regulating apparatus 4 in which the resistance to gas flow is adjusted to the same value with that in the catalyst vessel 2, apparatus 4 consisting of either a dummy vessel containing inactive particles or a capillary tube, and then to the FID detector 5 for measuring total hydrocarbon content of the gas sample. Then, substraction procedure of methane content from total hydrocarbon content is performed by the calculator 6 to indicate the content of hydrocarbons other than methane in the indicator 7. Accordingly, the concentration of hydrocarbons other than methane is continuously measured by the device of the present invention.

Figure 2:
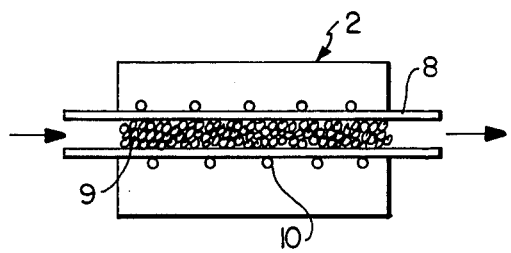
FIG. 2 is a cross-sectional view of a vessel containing catalyst.

Referring to the embodiment of the invention, FIG. 2 is a cross-sectional view of a catalyst vessel 2, in which reference numeral 8 is a column, 9 is a catalyst in the column 8, and 10 is an electric wire.

In the practice of the invention, there is employed a column type catalyst vessel which consists of a column 8 and catalyst 9. The column 8 requires length of 150 to 500 $mm$ and this type of column is suitable for measuring small concentrations of hydrocarbon such as several ten ppm etc. The whole column system should be maintained at a temperature from 100° C to 200° C (the range of temperature regulation is within ± 1° C) and the amount of sample gas treated in the column is preferably less than 1$l$.

Now, let us further describe the catalyst used in the present invention. For the purpose of the present invention it is prefered to use a catalyst, which has a large absorbing power, excellent acid-resistance and water-resistance, and high mechanical strength, the catalyst being shape-stable to boiling or charging procedure and of heat resistance to high temperatures such as above 300° C.

The catalysts suitable for the present purpose are illustrated by the following examples according to the invention.

1. Catalyst which is composed of active carbon particles whose outer particle surface and inner surface of holes therein are coated with platinum to about 10 %, by weight.

2. Catalyst which is composed of active carbon particles whose outer surface and inner surface of pores therein are coated with platinum of about 10 %, by weight and a small amount (for example, 0.5 to 1 %, by weight) of additive, such as palladium, or the mixture of palladium and molybdenum.

For oxidizing ethane and propane, catalyst (2) is more effective than catalyst (1). However, when an additive is in excess of an amount described above, methane is also oxidized.

3. Catalyst which is composed of synthetic zeolite having effective inner pore diameter of 10A (molecular sieve 13x,), whose outer surface and inner surface pores therein are coated with platinum to about 10 %, by weight.

4. Catalyst which is composed of synthetic zeolite having effective inner pore diameter of 10A (molecular sieve 13x,), whose outer surface and inner surface pores therein are coated with platinum of about 10 %, by weight and a small amount (several percent, by weight) of additive described in preceding paragraph, (2). In the preparation of above catalysts, 1. it is preferred that particle of active carbon used as the catalyst carrier be of spherical shape (0.5 to 1.0$^{mm}$ in diameter is suitable for the present purpose) and further be of uniform size, or 2. it is preferred that there be employed synthetic zeolite of spherical shape and uniform particle size distribution.

For example, the above catalyst composed of active carbon coated with platinum is prepared by the following procedure.

1. The active carbon particles are sieved to obtain the particles of 0.5 to 1.0 mm in size and are washed with water to remove impurities. After washing the active carbon obtained is well dried in a dry air atmosphere.

2. Then a certain amount of platinum acid is weighed out and dissolved in water, the resulting solution being poured on to the pre-weighed above-described active carbon. The amount of water to be added is preferably twice the amount of active carbon.

3. Then the treated active carbon is boiled using a water bath to evaporate water followed by reducing the pressure to several torr with a vacuum pump.

4. After the vacuum-impregnation procedure, the active carbon powder is subjected to vacuum-drying.

5. The dried active carbon is caclined at a temperature of 300° to 400° C for at least 3 hours.

6. The calcined catalyst is washed well with water to remove remaining acid.

7. The catalyst after water-washing is dried in an inert gas atmosphere such as nitrogen gas at room temperature or at an elevated temperature with heating to give the final catalyst product.

Figure 3:
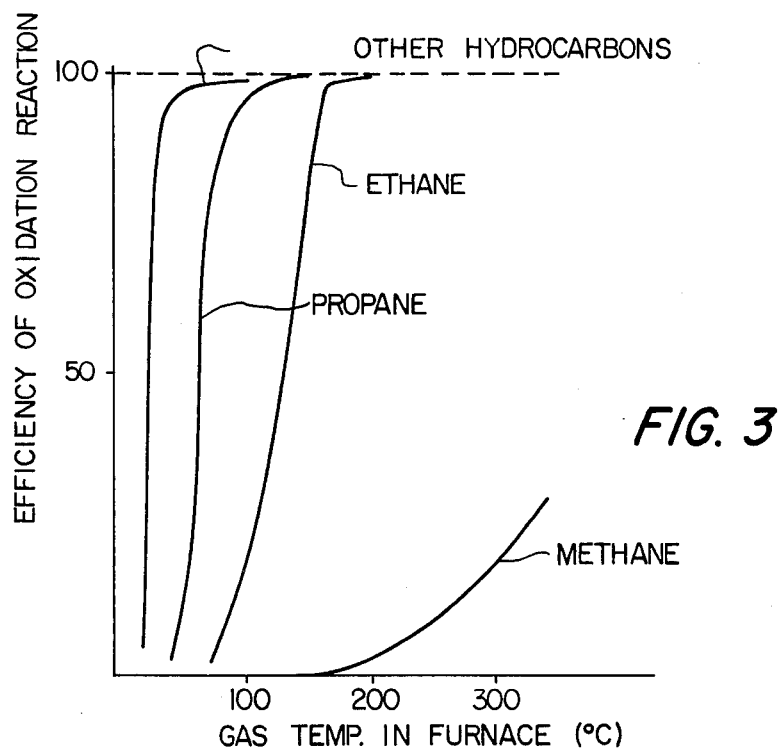
FIG. 3 is a graph showing relationship between hydrocarbon temperature and efficiency of oxidation in the practice of the invention.

The experimental results obtained by the separation of the present invention are shown in FIG. 3.

As can be seen from the FIG. 3, hydrocarbons other than methane, ethane and propane were separated up to about 100 % and ethane and propane were separated off up to about 99%. In the above process, the separation of hydrocrbons other than methane, ethane and propane is carried out based on the difference of oxidation reaction temperature and the separation of ethane and propane from methane is considered to be based on the following mechanism.

For example, let us explain the case employing the catalyst composed of active carbon coated with platinum. A gas mixture of methane, ethane and propane is contacted with the catalyst, ethane and propane being absorbed on the surface of the catalyst as soon as the gas is contacted therewith. The ethane and the propane are oxidized by the action of catalyst when absorbed thereon. On the other hand, the oxidation rate of methane is a little lower than that of ethane and propane. Although methane is absorbed on the catalyst, the desorption of methane takes place at higher rate than oxidation process does. Therefore, methane can be separated from ethane and propane.

Thus, the present invention provides new method in that methane is separated with high efficiency from hydrocarbons other than methane. When applying the method of the invention to the hydrocarbon measuring device for monitoring atmospheric air pollution, the precision of the measurements can be much improved.

Figure 4:
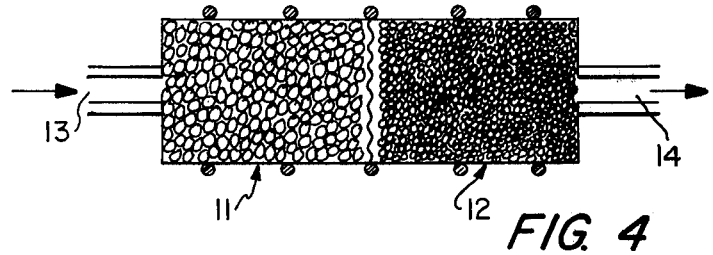
FIG. 4 illustrates a cross-sectional view of another example of the invention.

In FIG. 4, an example is given to further illustrate this invention.

Referring now to the drawing, there is shown two consecutively-placed vessels containing catalyst, the first catalyst vessel being filled with commercially available catalyst (for example, molecular sieve, 4A coated with platinum and molybdenum), which is kept at a temperature of about 170° C and the second catalyst vessel 12 being filled with a catalyst having high absorption efficiency, prepared by the procedure above-described, (for example, active carbon coated with platinum and molybdenum), which is also kept at a temperature of about 170° C and the sample gas being introduced from inlet 13 and discharged from exit 14 after passing through two catalyst vessels. In the first catalyst vessel 11, hydrocarbons other than methane, ethane or propane are removed at about 90 % and in the second catalyst vessel 12, remaining hydrocarbons other than methane, ethane or propane, ethane and propane are removed by the oxidation process.

The above system is particularly suitable for the case when the content of hydrocarbon in a sample gas is high. Since most of the hydrocarbons other than methane, ethane and propane are removed by oxidation in the first catalyst vessel 11 and the sample gas treated in the first vessel, then introduced into the second catalyst vessel contains a very small amount of such hydrocarbons the life of the catalyst contained in the second vessel 12 is considerably increased and thus separation of methane from other hydrocarbons than methane can be performed at high efficiency.

In another embodiment of the invention, there may be introduced only one part sample gas after passing through the first catalyst vessel 11 (for example, several hundreds ml in 3000 ml of initial amount), into the second catalyst vessel 12.

Further, in the practice of this invention, oxidation of methane can be effectively suppressed by adding moisture. When a sample is atmospheric air, however there is no need to deliberately add moisture to the sample.

What is claimed is:

1. A method for the separation of methane from a gaseous mixture containing methane and at least one of ethane and propane which comprises
    a. simultaneously passing said gaseous mixture and oxygen over a catalyst comprising platinum on an active carbon carrier;
    b. selectively oxidizing the ethane and propane in said gaseous mixture at a temperature of about 170° C and
    c. recovering methane from said mixture.

2. A method according to claim 1 wherein said catalyst is in the form of spheroidal particles.

3. A method according to claim 2 wherein said particles are 0.5 to 1.0 mm. in diameter.

4. A method according to claim 1 wherein said catalyst contains platinum in an amount of about 10% by weight.

5. A method according to claim 1 wherein said catalyst further comprises palladium in an amount of about 0.5 to 1% by weight.

6. A method according to claim 4 wherein said catalyst further comprises palladium in an amount of about 0.5 to 1% by weight.

7. A method according to claim 1 wherein said gaseous mixture additionally contains hydrocarbons other than methane, ethane and propane and wherein said hydrocarbons are more readily oxidized than methane, ethane and propane, which method comprises selectively oxidizing said hydrocarbons other than methane, ethane and propane in a first reaction vessel to obtain an effluent containing methane, ethane and propane and then selectively oxidizng said ethane and propane in a second reaction vessel.

* * * * *